(12) United States Patent
Cawley

(10) Patent No.: US 8,012,145 B2
(45) Date of Patent: Sep. 6, 2011

(54) MEDICAL HUB HAVING TRANSPARENT OBSERVATION SECTION

(75) Inventor: Neil Cawley, Maretta, GA (US)

(73) Assignee: Volcano Corporation, Rancho Cordova, CA (US)

( * ) Notice: Subject to any disclaimer, the term of this patent is extended or adjusted under 35 U.S.C. 154(b) by 745 days.

(21) Appl. No.: 11/118,129

(22) Filed: Apr. 29, 2005

(65) Prior Publication Data

US 2006/0116660 A1    Jun. 1, 2006

Related U.S. Application Data

(60) Provisional application No. 60/567,260, filed on Apr. 30, 2004.

(51) Int. Cl.
G01F 23/02 (2006.01)
A61M 25/16 (2006.01)
A61M 25/18 (2006.01)
A61M 39/00 (2006.01)
A61M 39/10 (2006.01)

(52) U.S. Cl. ......................................... 604/533; 73/327

(58) Field of Classification Search ............. 604/164.07, 604/167.05, 168.01, 246, 533, 534, 538; 359/804, 441, 442; 116/264, 274; 73/323, 73/327

See application file for complete search history.

(56) References Cited

U.S. PATENT DOCUMENTS

| | | | |
|---|---|---|---|
| RE15,782 E * | 3/1924 | Gross | 362/540 |
| 4,435,094 A * | 3/1984 | Shapiro | 374/191 |
| 4,633,863 A | 1/1987 | Filips et al. | |
| 4,713,061 A | 12/1987 | Tarello et al. | |
| 4,745,877 A * | 5/1988 | Chang | 116/274 |
| 5,030,207 A * | 7/1991 | Mersch et al. | 604/168.01 |
| 5,112,313 A | 5/1992 | Sallee | |
| 5,372,589 A | 12/1994 | Davis | |
| 5,423,750 A | 6/1995 | Spiller | |
| 5,649,874 A * | 7/1997 | Headford et al. | 473/569 |
| 6,386,196 B1 * | 5/2002 | Culton | 128/205.23 |
| 6,482,186 B1 | 11/2002 | Douglas et al. | |
| 6,533,759 B1 * | 3/2003 | Watson et al. | 604/167.02 |
| 6,656,161 B2 * | 12/2003 | Young et al. | 604/168.01 |
| 2002/0026127 A1 * | 2/2002 | Balbierz et al. | 600/567 |

FOREIGN PATENT DOCUMENTS

EP        139872 A1 *   5/1985

* cited by examiner

Primary Examiner — Kevin C Sirmons
Assistant Examiner — Bradley J Osinski
(74) Attorney, Agent, or Firm — Jeffrey L. Thompson; Thompson & Thompson, P.A.

(57) ABSTRACT

A medical hub for connecting a tubular member to a fluid source has a first structure for connecting to the fluid source, a second structure for connecting to the tubular member, and a transparent portion formed between the first and second structures. The transparent portion in one embodiment has a generally spherical shape that allows visual monitoring of a fluid flowing through the hub from a wide viewing angle. The transparent portion can be formed of clear plastic or other suitable optical material that magnifies an image of the fluid flowing through the hub. Other embodiments are described in which the transparent portion has a cylindrical shape, a square shape, a multifaceted shape, and a combination of such shapes. The tubular member can be a catheter or other intravenous tubing.

15 Claims, 2 Drawing Sheets

MEDICAL HUB HAVING TRANSPARENT OBSERVATION SECTION

RELATED APPLICATIONS

This application claims the benefit of the Applicant's provisional patent application No. 60/567,260 filed on Apr. 30, 2004.

BACKGROUND OF THE INVENTION

1. Field of the Invention

The present invention relates generally to medical devices and, in particular, to medical hubs and other devices having transparent sections for observing fluid flowing therethrough.

2. Description of the Related Art

The administration of liquid medications and nutrients to patients via intravenous administration is a well-established medical practice. Typically, the nutrient or medication solution is delivered into the patient's bloodstream directly from an intravenous fluid line. Intravenous fluid lines generally consist of a flexible plastic tubing that connects via a hub directly with the source of the intravenous fluid. The fluid source is commonly an elevated intravenous fluid storage container that can be of flexible wall plastic construction, for example. In such a typical system, the flow of intravenous fluid to the patient is gravity driven. However, the intravenous fluid may also be pumped into the patient.

Catheters are also commonly used to deliver therapeutic and diagnostic fluids to selected locations within a patient's body. For example, it is common during the use of stents to use catheters to apply fluid-based drugs to the site of the dilated lesion to prevent or reduce chances of restenosis and to aid in the healing of flaps, dissection or other hemorrhagic conditions that may appear after an angioplasty procedure. Numerous other examples of the use of catheters to deliver fluids intravenously will also be known to those skilled in the art.

Quality control is a necessary and vital component of the administration of intravenous fluids. The health care provider typically monitors the quality of the intravenous fluid administration by visually examining the fluid in the intravenous fluid container and/or the fluid in the intravenous tubings and catheters as the fluid enters the patient's body. By monitoring the course of the infusion, the medical care provider can sometimes detect problems with the quality of the intravenous fluid or the process of administering the fluid. For example, the visual monitoring of the intravenous fluid reservoir or the tubing can sometimes provide an indication of the clarity of the fluid, the presence of contaminants, precipitation, and so forth.

However, in many cases, it is difficult to provide adequate quality control by visual monitoring because the fluid container and/or the catheter or tubing are opaque, or because the quality problems are too small to notice with the naked eye. Thus, there is a need in the industry for a device that would enhance the visual monitoring of fluids being administered intravenously.

SUMMARY OF THE INVENTION

It is an object of the present invention to provide a device for enhancing the visual observation of fluids being administered intravenously.

It is a further object of the present invention to provide an improved medical hub for connecting a catheter or other tubing to a container of fluid to be administered, whereby the hub has an observation section that magnifies the fluid being administered and provides a wide viewing angle or multiple viewing angles for visual monitoring.

To achieve these and other objects of the present invention, a medical hub for connecting a tubular member to a fluid source has a first structure for connecting to the fluid source, a second structure for connecting to the tubular member, and a transparent portion formed between the first and second structures. The transparent portion in one embodiment has a generally spherical shape that allows visual monitoring of a fluid flowing through the hub from a wide viewing angle. The transparent portion can be formed of clear plastic or other suitable optical material that magnifies an image of the fluid flowing through the hub. In other embodiments, the transparent portion has a generally cylindrical shape, a generally square shape, a multifaceted shape, and a combination of such shapes. The tubular member can be a catheter or other intravenous tubing.

According to a broad aspect of the invention, a hub for connecting a tubular member to a fluid source is provided, comprising: a first structure for connecting to the fluid source; a second structure for connecting to the tubular member; and a transparent portion formed between the first and second structures that allows visual monitoring of a fluid flowing through the hub.

According to another broad aspect of the present invention, a combination of a medical hub and a tubular member connected to the medical hub is provided, with the medical hub, comprising: a connecting structure for connecting the hub to a fluid source; and a transparent portion formed in the hub that allows visual monitoring of a fluid flowing through the hub.

Additional objects, advantages, and novel features of the invention will be set forth in the following description, and will become apparent to those skilled in the art upon reading this description or practicing the invention. The objects and advantages of the invention may be realized and attained by the appended claims.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

Figure 1:
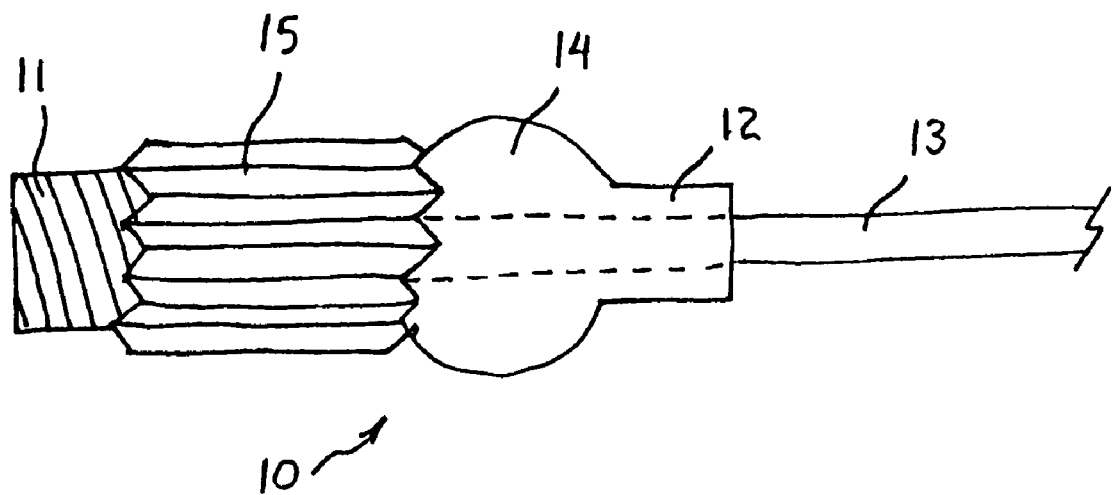
FIG. 1 is a side view of a catheter connected to a medical hub having a generally spherical observation section according to the present invention.

A medical hub having an observation section for visual monitoring according to the present invention will now be described with reference to FIGS. 1 to 2 of the accompanying drawings.

The medical hub 10 has a first structure 11 for connecting to a fluid source (not shown). The fluid source can be a conventional fluid storage container, an outlet of a pump for administering the fluid, or a variety of other fluid sources known to those skilled in the art. The first structure 11 can be a male threaded portion of a threaded connector, as shown in the drawings. The male threaded portion 11 is adapted to be received in a mating female threaded part (not shown) of the fluid source in a known manner.

The hub 10 has a second structure 12 for connecting to the tubular member 13. The tubular member 13 can be an intravenous tubing commonly used to deliver nutrient or medication fluids to a patient's bloodstream, or a catheter commonly used to apply fluids to selected locations within a patient's body. The second structure 12 for connecting to the tubular member 13 can be a glued, welded, barbed, crimped, or flared fitting, or any other conventional structure for connecting tubular members to a hub.

The hub 10 has a transparent portion 14 formed between the first and second structures 11, 12. The transparent portion 14 completely surrounds a tubular lumen of the hub and allows visual monitoring of a fluid flowing through the hub 10. For example, a nongaseous fluid can be inspected and monitored for the presence of bubbles and impurities.

Figure 2:
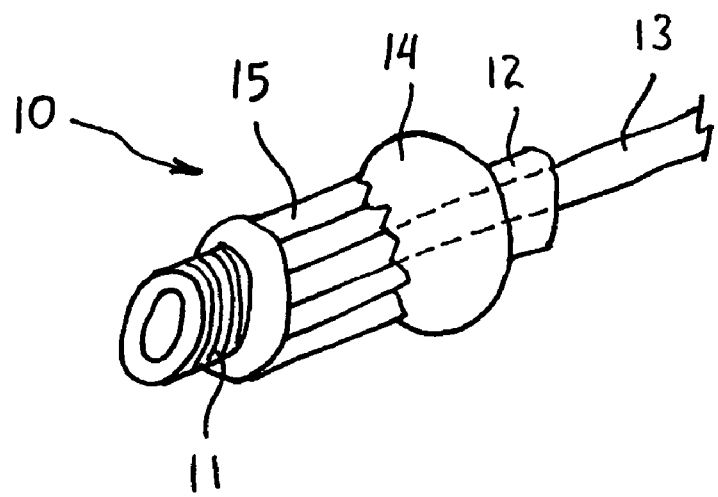
FIG. 2 is a perspective view of the catheter and medical hub shown in FIG. 1.

The transparent portion 14 shown in FIGS. 1 and 2 has an enlarged bulbous shape, which can be generally spherical. The bulbous shape of the transparent portion 14 functions to magnify an image of the fluid flowing through the hub 10. The transparent portion 14 can be made of an optical material, such as a material commonly used for plastic optical lenses, to further enhance the magnification.

Moreover, since the transparent portion 14 is spherical, the fluid flowing through the hub 10 can be viewed from a wide viewing angle at virtually any orientation of the hub 10. The combination of the wide viewing angle and the magnification properties of the transparent portion 14 makes visual monitoring of the flowing fluid during use of the hub 10 convenient and highly effective.

The hub 10 also includes a gripping portion 15 having a rough surface formed between the first structure 11 and the transparent portion 14. The gripping portion 15 includes a rough surface 16 that can be easily gripped by a health care provider's fingers for turning the threaded portion 11 of the hub into mating engagement with the corresponding structure (not shown) of the fluid source.

The hub 10 can be formed as an integral molded unit. In this case, the first and second structures 11 and 12, the gripping portion 15, and the transparent portion 14 are all molded together in one molding operation from the same material. Alternatively, one or more of the components of the hub 10 can be formed separately and secured together with the other components by welding or bonding with an adhesive. As explained above, the tubular member 13 can also be permanently connected to the hub 10 by welding, adhesive, or other suitable means.

Figure 3:
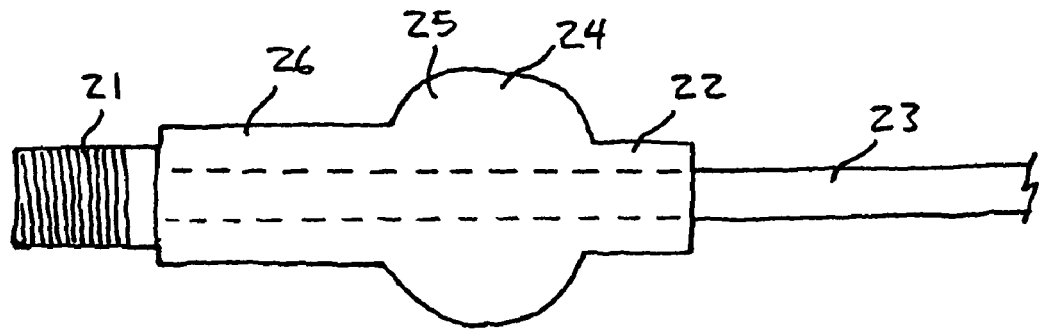
FIG. 3 is a side view of a catheter connected to a medical hub having a generally spherical observation section and a cylindrical observation section according to another embodiment of the present invention.

FIG. 3 shows a hub 20 according to another embodiment of the present invention. As with the first embodiment described above, the hub 20 has a first structure 21 for connecting to a fluid source, a second structure 22 for connecting to a tubular member 23, such as an intravenous tubing or a catheter, and a transparent portion 24 formed between the first and second structures 21, 22. The transparent portion 24 allows visual monitoring of a fluid flowing through the hub 20. For example, the fluid can be inspected and monitored for the presence of bubbles and impurities.

The transparent portion 24 has a first bulbous portion 25 having a generally spherical shape and a second portion 26 having a generally cylindrical shape. The shape of the first transparent portion 25 functions to magnify an image of the fluid flowing through the hub 20 and can be viewed from multiple viewing angles. The shape of the second transparent portion 26 also functions to magnify an image of the fluid flowing through the hub 20 and can be viewed from multiple viewing angles. The combination of the shapes of the first and second transparent portions 25, 26 allows the hub 20 to function well in a wider variety of viewing conditions. For example, in certain lighting, the cylindrical shaped portion 26 will provide better visibility of the fluid flowing through the hub 20 than the spherical shaped portion 25. The transparent portions 25, 26 can be made of optical materials, such as materials commonly used for plastic optical lenses, to further enhance the magnification.

The hub 20 can be formed as an integral molded unit or as separate elements secured together, similar to the construction of the hub 10 explained above.

Figure 4:
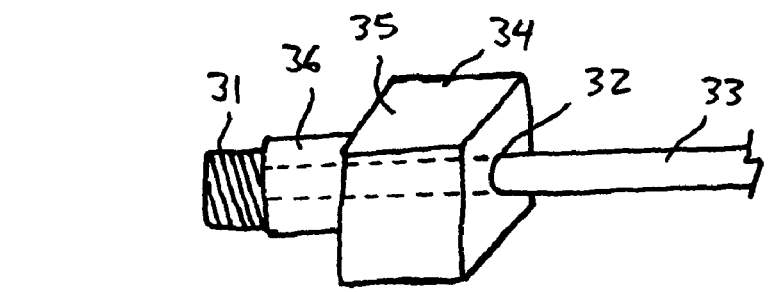
FIG. 4 is a perspective view of a catheter connected to a medical hub having a generally square observation section and a cylindrical observation section according to another embodiment of the present invention.

FIG. 4 shows a hub 30 according to another embodiment of the present invention. As with the other embodiments described above, the hub 30 has a first structure 31 for connecting to a fluid source, a second structure 32 for connecting to a tubular member 33, such as an intravenous tubing or a catheter, and a transparent portion 34 formed between or as part of the first and second structures 31, 32. The transparent portion 34 allows visual monitoring of a fluid flowing through the hub 30. For example, the fluid can be inspected and monitored for the presence of bubbles and impurities.

The transparent portion 34 has a first generally square-shaped portion 35 and a second generally cylindrical-shaped portion 36. The shape of the first transparent portion 35 functions to magnify an image of the fluid flowing through the hub 30 and can be viewed from multiple viewing angles. The shape of the second transparent portion 36 also functions to magnify an image of the fluid flowing through the hub 30 and can be viewed from multiple viewing angles. The combination of the shapes of the first and second transparent portions 35, 36 allows the hub 30 to function well in a wider variety of viewing conditions. For example, in certain lighting, the square-shaped portion 36 will provide better visibility of the fluid flowing through the hub 30 than the spherical shaped portion 35. The transparent portions 35, 36 can be made of optical materials, such as materials commonly used for plastic optical lenses, to further enhance the magnification.

Figure 5:
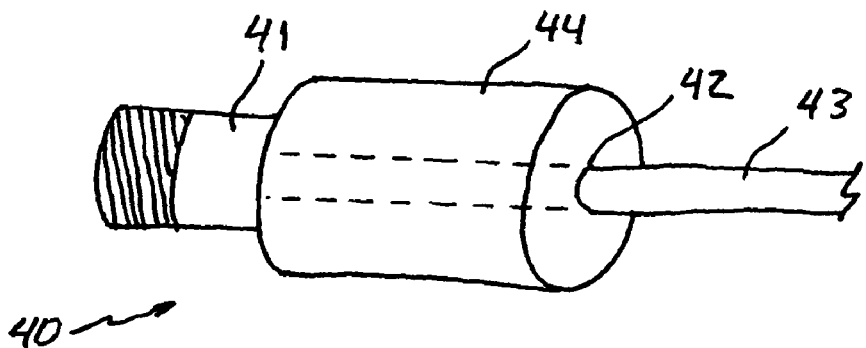
FIG. 5 is a perspective view of a catheter connected to a medical hub having a generally cylindrical observation section according to another embodiment of the present invention.

FIG. 5 shows a hub 40 according to another embodiment of the present invention. As with the other embodiments described above, the hub 40 has a first structure 41 for connecting to a fluid source, a second structure 42 for connecting to a tubular member 43, such as an intravenous tubing or a catheter, and a transparent portion 44 formed between or as part of the first and second structures 41, 42. The transparent portion 44 allows visual monitoring of a fluid flowing through the hub 40. For example, the fluid can be inspected and monitored for the presence of bubbles and impurities.

The transparent portion 44 has a substantially smooth and continuous outer surface, such as a generally cylindrical shape, and functions to magnify an image of the fluid flowing through the hub 30. As with the transparent portions of the other embodiments described above, the cylindrical-shaped transparent portion 44 can be viewed from multiple viewing angles and under a variety of lighting conditions. The transparent portion 44 can be made of optical materials, such as materials commonly used for plastic optical lenses, to further enhance the magnification.

The hubs 30, 40 described above can be formed as an integral molded unit or as separate elements secured together, as in the construction of the hub 10 explained above.

Another embodiment of the present invention (not shown) provides a hub having a transparent section with a multifaceted bulbous shape. The multifaceted shape allows the fluid flowing through the hub to be viewed from multiple viewing angles and under a variety of lighting conditions. With any of the embodiments described above, a spectral coating can be applied to the transparent section of the hub to help break up the light and make it easier to view the fluid flowing through the hub without glare from the ambient lighting.

While the invention has been specifically described in connection with specific embodiments thereof, it is to be understood that this is by way of illustration and not of limitation, and the scope of the appended claims should be construed as broadly as the prior art will permit.

What is claimed is:

1. A hub for connecting a tubular member to a nongaseous fluid source, comprising:
    a first structure for connecting to the nongaseous fluid source;
    a second structure for connecting to the tubular member; and
    a transparent portion formed between said first and second structures that allows visual inspection and monitoring for the presence of bubbles and impurities in a nongaseous fluid flowing through a tubular lumen of the hub;
    wherein said first and second structures and said transparent portion are molded together as an integral molded unit, and said transparent portion has a generally spherical shape that completely surrounds said tubular lumen of the hub and magnifies an image of the nongaseous fluid flowing through the hub.

2. The hub according to claim 1, wherein said transparent portion is formed of an optical material that magnifies an image of the fluid flowing through the hub.

3. The hub according to claim 1, wherein said tubular member is a catheter.

4. The hub according to claim 1, wherein said first structure comprises a threaded connector.

5. The hub according to claim 1, further comprising a gripping portion having a rough surface formed between said first structure and said second structure to facilitate rotating the hub during connection to a fluid source.

6. The hub according to claim 1, wherein said transparent portion comprises a multifaceted bulbous shape.

7. The hub according to claim 1, wherein said transparent portion comprises a spectral coating to reduce glare from ambient lighting.

8. In combination, a medical hub and a tubular member connected to said medical hub, said medical hub, comprising:
    a connecting structure for connecting said hub to a nongaseous fluid source; and
    a transparent portion formed in said hub that allows visual inspection and monitoring for the presence of bubbles and impurities in a nongaseous fluid flowing through a tubular lumen of said hub;
    wherein said connecting structure and said transparent portion are molded together as an integral molded unit, and said transparent portion has a generally spherical shape that completely surrounds said cylindrical lumen of the hub and magnifies an image of the nongaseous fluid flowing through the hub.

9. The combination according to claim 6, wherein said transparent portion is formed of an optical material that magnifies an image of the fluid flowing through the hub.

10. The combination according to claim 6, wherein said connecting structure is a threaded connector.

11. The combination according to claim 6, wherein said hub further comprises a gripping portion having a rough surface formed between said connecting structure and said transparent portion to facilitate rotating said hub to engage the connecting structure.

12. The combination according to claim 6, wherein said tubular member is a catheter.

13. The combination according to claim 8, wherein said transparent portion comprises a first transparent portion having a smooth and continuous outer surface and a second transparent portion having a multifaceted outer surface, and wherein said first and second transparent portions both function to magnify an image of the fluid flowing through the hub.

14. The combination according to claim 8, wherein said transparent portion comprises a multifaceted bulbous shape.

15. The combination according to claim 8, wherein said transparent portion comprises a spectral coating to reduce glare from ambient lighting.

* * * * *